(12) United States Patent
Abribat et al.

(10) Patent No.: US 8,138,120 B2
(45) Date of Patent: Mar. 20, 2012

(54) MICROEMULSIONS AS ADJUVANTS FOR AGRICULTURAL CHEMICALS

(75) Inventors: Benoit Abribat, Saint Fargeau Ponthierry (FR); Frank Lachut, West Chester, OH (US); Timothy Anderson, Hamilton, OH (US); Michael Pompeo, Mason, OH (US); Dianne Michail, Brunswick (AU)

(73) Assignee: Cognis IP Management GmbH, Duesseldorf (DE)

( * ) Notice: Subject to any disclaimer, the term of this patent is extended or adjusted under 35 U.S.C. 154(b) by 308 days.

(21) Appl. No.: 10/796,697

(22) Filed: Mar. 9, 2004

(65) Prior Publication Data
US 2004/0235668 A1 Nov. 25, 2004

Related U.S. Application Data

(60) Provisional application No. 60/453,768, filed on Mar. 11, 2003.

(51) Int. Cl.
*A01N 25/00* (2006.01)
(52) U.S. Cl. .................................... 504/116.1
(58) Field of Classification Search .............. 504/362, 504/206, 363; 514/938, 53, 72, 204; 516/53, 516/72, 204
See application file for complete search history.

(56) References Cited

U.S. PATENT DOCUMENTS

| 5,266,690 A | | 11/1993 | McCurry, Jr. et al. | |
|---|---|---|---|---|
| 5,538,662 A | * | 7/1996 | Klier et al. | 510/284 |
| 5,905,072 A | * | 5/1999 | Capuzzi et al. | 514/63 |
| 6,255,253 B1 | * | 7/2001 | Foerster et al. | 504/363 |
| 6,586,366 B1 | * | 7/2003 | Auda et al. | 510/242 |
| 6,586,479 B2 | * | 7/2003 | Miller et al. | 516/73 |

FOREIGN PATENT DOCUMENTS

| CN | 1052302 | * | 11/1989 |
|---|---|---|---|
| JP | 04046104 | * | 2/1992 |
| SU | 450563 | * | 4/1975 |

OTHER PUBLICATIONS

Tetraconazole (Ref: M 14360), PPDB, circa 1990, pp. 1-9.*
Kirk-Othmer Encyclopedia of Chemical Technology, 3rd Ed., vol. 22, John Wiley & Sons, (1983), pp. 360-361.
Editor: C D S Tomlin: BCBP: A World Compendium. The Pesticide Manual. Fourteenth Edition -.

* cited by examiner

*Primary Examiner* — Alton Pryor
(74) *Attorney, Agent, or Firm* — Diehl Servilla LLC

(57) ABSTRACT

A microemulsion composition is provided for use as an adjuvant with agrochemicals, comprising an oil phase component, a hydrophilic emulsifier, a lipophilic co-emulsifier and water.

12 Claims, No Drawings

MICROEMULSIONS AS ADJUVANTS FOR AGRICULTURAL CHEMICALS

CROSS-REFERENCE TO RELATED APPLICATIONS

This application claims the benefit of copending provisional application Ser. No. 60/453,768, filed on Mar. 11, 2003, the entire contents of which is incorporated herein by reference.

BACKGROUND OF THE INVENTION

The invention relates to liquid adjuvants, in the form of microemulsions, which may be combined with agricultural chemicals to improve the efficacy thereof.

Agrochemicals such as, for example, biocides, herbicides, insecticides and even fertilizers contain organic compounds which are insoluble or poorly soluble in water. In order to convert these agrochemicals into a form in which they are easy to handle by the user, they are often marketed as concentrated solutions in suitable organic solvents, for example alkyl benzene. Before use, these solutions have to be diluted to their required concentrations. However, the use of these organic solvents is undesirable for economic reasons and above all for ecological reasons. Accordingly, there is a need for water-based concentrates of the agrochemicals in question.

Generally, microemulsions are isotropic, thermodynamically stable mixtures comprising oil, water and an emulsifier, and, optionally, additives which may include alcohols and electrolytes. The emulsifier commonly comprises alkoxylated non-ionic surfactants, e.g., ethylene oxide, propylene oxide and mixtures thereof, which will prevent the microemulsion from breaking down to separated oil and water based phases within a relatively limited temperature range.

Microemulsions of this type have served the pesticide industry in the form of ready to use adjuvant products for use with agricultural chemicals (agrochemicals) for a number of years. The fine droplet size (typically as small as about 100 nm) of these emulsions results in clear, transparent products with long shelf lives. The water component of the microemulsion typically replaces a significant portion of the hydrocarbon solvents normally used with hydrophobic agrochemical concentrates, resulting in environmentally friendly formulations. However, these microemulsions contain a large amount of surfactants based on ethylene and propylene oxide block copolymers, which are poorly biodegradable and phytotoxic to plants. Furthermore, these block copolymers possess a cloud point, a well known property of block copolymers and nonionic surfactants which is the result of the surfactant becoming less soluble with increasing temperature; the temperature at which the appearance of a second phase is observable is the "cloud point" (see Kirk Othmer's Encyclopedia of Chemical Technology, $3^{rd}$ ed. Vol. 22, pp. 360-361 (John Wiley & Sons, 1983)). Accordingly, if the temperature of the microemulsion reaches the cloud point, the microemulsion will be unstable.

U.S. Pat. No. 6,255,253 to Foerster et al. discloses a microemulsion formulation including water, an emulsifier, and an oil phase comprising a water-insoluble agrochemical, i.e., the oil droplets in the microemulsion comprise the agrochemical component. In this type of mixture the water-insoluble agrochemicals are put into a microemulsion with the emulsifier(s) and water so that they are essentially ready for use, though they are typically diluted before being applied in the field.

However, it is often convenient to maintain separate stocks of agrochemical and adjuvant and combine them, with additional water, just prior to their application in the field. Further, it is preferable for an adjuvant to be suitable for use with a number of different agrochemicals which may be chosen by the user, not just oil based agrochemicals.

Accordingly, it would be advantageous to have an ecologically safe, temperature stable microemulsion which may be mixed with water-soluble, substantially water-soluble, water-insoluble, or substantially water-insoluble agrochemicals shortly before their application and which will increase the efficacy thereof.

BRIEF SUMMARY OF THE INVENTION

The invention is a microemulsion for use as an adjuvant with agrochemicals comprising an oil phase component, a hydrophilic emulsifier, a lipophilic co-emulsifier, and water. The microemulsions which result are clear liquids with droplet particle sizes which are generally less than 100 nanometers.

In accordance with a preferred embodiment of the invention, the oil phase component is an ester, most preferably a methyl ester, the hydrophilic emulsifier is an alkyl polyglycoside, and the lipophilic co-emulsifier is a glycerol ester or sorbitan ester possessing 6 to 22 carbon atoms, most preferably glycerol monooleate or sorbitan monolaurate. Agrochemicals suitable for use with the microemulsion adjuvant preferably include herbicides and other substances used for plant protection, such as pesticides, herbicides, algicides, fungicides, bactericides, viricides, insecticides, aphicides, miticides, nematicides, molluscicides, and the like), plant growth regulators, fertilizers and nutrients, gametocides, defoliants, desiccants, pest repellants, synergists, herbicide safeners (which reduce the phytotoxicity of herbicides to crop plants), salt additives (which enhance the effects of herbicides), preservatives, mixtures thereof, and the like.

The microemulsion adjuvant of the present invention is preferably combined with a water-soluble or substantially water-soluble agrochemical at the time of application in the field. The microemulsion adjuvant of the present invention may optionally include other typical additives for agrochemical applications.

Microemulsions of the invention have been found to increase the efficacy of agrochemicals in field trials. Furthermore, formulations of the adjuvant may have additional advantages, including (1) all components of the microemulsion adjuvant may be naturally derived and, thus, are readily biodegradable; (2) components of the microemulsion may all be "green" chemicals, i.e., no special labeling is required; and (3) the components of the microemulsion may reduce foam formation during application of the agrochemical without the need for including additional defoaming chemicals in the adjuvant.

DETAILED DESCRIPTION OF THE INVENTION

The present invention relates to liquid adjuvants, in microemulsion form, which may be combined with agrochemicals to improve the efficacy of the agrochemicals.

As used herein, the term "agrochemical" includes any pesticides, herbicides, chemicals and microbial agents used as active ingredients of products for control of crop and lawn pests and diseases, animal ectoparasites, and other pests in public health. An agrochemical is any substance, whether naturally or synthetically derived, which (a) has biological activity or is capable of releasing in a plant an ion, moiety or derivative which has biological activity, and (b) is applied to a plant with the intent or result that the substance or its biologically active ion, moiety or derivative enter living cells or tissues of the plant and elicit a stimulatory, inhibitory, regulatory, therapeutic, toxic or lethal response in the plant itself, or enter living cells or tissues of a pathogen, parasite or feeding organism present in or on the plant to elicit an inhibitory, toxic or lethal response. Examples of agrochemicals include, but are not limited to, chemical pesticides (such as herbicides, algicides, fungicides, bactericides, viricides, insecticides, aphicides, miticides, nematicides, molluscicides, and the like), plant growth regulators, fertilizers and nutrients, gametocides, defoliants, desiccants, pest repellants, synergists, herbicide safeners (which reduce the phytotoxicity of herbicides to crop plants), salt additives (which enhance the effects of herbicides), preservatives, mixtures thereof, and the like.

The microemulsion contains an oil phase component, a hydrophilic emulsifier, a lipophilic co-emulsifier, and water. Other additives typical for agrochemical applications may also be included.

Suitable oil phase components include, but are not limited to, hydrocarbons and fatty acid esters that are liquid at room temperature. Suitable hydrocarbons include, for example, mineral oils, vegetable oils, silicone oils, paraffin oils, liquid polyolefins and alkyl cyclohexanes, for example 1,3-diisooctyl cyclohexane. Suitable fatty acid esters include, for example, the methyl and isopropyl esters of fatty acids containing 12 to 22 carbon atoms, for example methyl laurate, methyl stearate, methyl oleate, methyl erucate, isopropyl palmitate, isopropyl stearate, isopropyl oleate.

Other suitable oil phase components are n-butyl stearate, n-hexyl laurate, n-decyl oleate, isooctyl stearate, isononyl palmitate, isononyl isononanoate, 2-ethylhexyl palmitate, 2-ethylhexyl laurate, 2-hexyldecyl stearate, 2-octyl dodecyl palmitate, oleyl oleate, oleyl erucate, erucyl oleate and esters obtainable from aliphatic alcohol mixtures and aliphatic carboxylic acids, for example esters of saturated and unsaturated fatty alcohols containing 12 to 22 carbon atoms and saturated and unsaturated fatty acids containing 12 to 22 carbon atoms which are obtainable from animal and vegetable fats. Naturally occurring liquid wax esters as present in sperm oil and jojoba oil are also suitable in the present invention.

Suitable oil phase components also include dicarboxylic acid esters such as, for example, di-n-butyl adipate, di-n-butyl sebacate, di-(2-ethylhexyl)-adipate, di-(2-ethylhexyl)-succinate, diisotridecyl azelate and diol esters such as, for example, ethylene glycol dioleate, ethylene glycol diisotridecanoate, propylene glycol di-(2-ethylhexanoate), butanediol diisostearate or neopentyl glycol dicaprylate.

Liquid triglycerides may also be used as oil phase components. Such triglycerides include, for example, olive, oil, sunflower oil, soybean oil, peanut oil, rapeseed oil, almond oil, palm oil or the liquid fractions of coconut oil or palm oil and also animal oils, for example neat's foot oil, the liquid fractions of beef tallow, or even synthetic triglyceride oils obtainable, for example, by esterification of glycerol with caprylic acid/capric acid mixtures, technical oleic acid or palmitic acid/oleic acid mixtures.

Preferably, the oil phase components of the invention are mineral oils, vegetable oils, paraffin oils, silicone oils, or esters, including fatty acid esters and methyl esters, most preferably methyl oleate or methyl laurate.

Hydrophilic emulsifiers for use in the present invention may include, for example, alkyl polyglycosides, e.g., alkyl (oligo)glycosides corresponding to the formula:

$$R\text{—}O\text{—}[Z]_x \qquad (I)$$

in which R is an alkyl group containing 8 to 22 carbon atoms, Z is a sugar unit containing 5 or 6 carbon atoms and x is a number of 1 to 10. The alkyl polyglycosides which can be used in the compositions and processes according to the invention are commercially available and sold, for example, as APG®, Glucopon®, Plantaren®, or Agnique® products from Cognis Corporation.

Examples of such alkyl polyglycosides include but are not limited to:

1. Agnique® PG 8107—an alkyl polyglycoside in which the alkyl group contains 8 to 10 carbon atoms and having an average degree of polymerization of 1.7.

2. APG® 425—an alkyl polyglycoside in which the alkyl group contains 8 to 16 carbon atoms and having an average degree of polymerization of 1.6.

3. APG® 625—an alkyl polyglycoside in which the alkyl group contains 12 to 16 carbon atoms and having an average degree of polymerization of 1.6.

4. APG® 300—an alkyl polyglycoside substantially the same as APG® 325 but having an average degree of polymerization of 1.4.

5. Agnique® PG 9116—an alkyl polyglycoside in which the alkyl group contains 9 to 11 carbon atoms and having an average degree of polymerization of 1.6.

6. Glucopon® 600—an alkyl polyglycoside in which the alkyl group contains 12 to 16 carbon atoms and having an average degree of polymerization of 1.4

7. Plantaren® 2000—a $C_{8-16}$ alkyl polyglycoside in which the alkyl group contains 8 to 16 carbon atoms and having an average degree of polymerization of 1.4.

8. Plantaren® 1300—a $C_{12-16}$ alkyl polyglycoside in which the alkyl group contains 12 to 16 carbon atoms and having an average degree of polymerization of 1.6.

9. Agnique® PG 8105—an alkyl polyglycoside in which the alkyl group contains 8 to 10 carbon atoms and having an average degree of polymerization of 1.5.

Other examples include alkyl polyglycoside surfactant compositions which are comprised of mixtures of compounds of formula I wherein Z represents a moiety derived from a reducing saccharide containing 5 or 6 carbon atoms; x is zero; and R is an alkyl radical having from 8 to 20 carbon atoms. The composition is characterized in that it has increased surfactant properties, an HLB in the range of from about 10 to about 16, and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglycosides, can be prepared by separation of the monoglycoside from the original reaction mixture of alkyl monoglycoside and alkyl polyglycosides after removal of the alcohol. This separation may be carried out by molecular distillation and normally results in the removal of about 70-95% by weight of the alkyl monoglycosides. After removal of the alkyl monoglycosides, the relative distribution of the various components, mono- and poly-glycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in U.S. Pat. No. 5,266,690, the entire contents of which are incorporated by reference herein.

Preferred alkyl polyglycosides are those in which the alkyl groups contain from 8 to 12 carbon atoms and have an average degree of polymerization of 1.6 to 1.7. The most preferred alkyl polyglycosides are those which have alkyl groups containing 8 to 10 carbon atoms and an average degree of polymerization of 1.7, and those which have alkyl groups containing 9 to 11 carbon atoms and an average degree of polymerization of 1.6

Lipophilic co-emulsifiers are known to those skilled in the art. Suitable lipophilic co-emulsifiers include, but are not limited to, fatty acid polyol partial esters, fatty alcohols or fatty alcohol polyol ethers.

Fatty acid polyol partial esters in the context of the invention are products of the esterification of fatty acids containing 8 to 22, preferably 12 to 22, carbon atoms with polyfunctional alcohols having a functionality of 3 to 10, preferably 3 to 6 and more preferably 3 or 4.

Particularly preferred fatty acid polyol partial esters are those in which only one OH function is esterified with a suitable fatty acid. The mixtures formed in such an esterification should advantageously contain 35 to 96% of monoesters, 1 to 50% of diesters and 0.1 to 20% of tri- or higher esters.

If glycerol is used as the polyol, the partial esters may be obtained particularly easily by transesterification of natural fats or oils with an excess of glycerol. Suitable natural fats and oils are, for example, beef tallow, lard, palm oil, sunflower oil or soybean oil, preferably natural fats or oils with a particularly high percentage content of oleic acid. Suitable polyols are, for example, propylene glycol, glycerol, erythritol trimethylol propane, pentaerythritol, sorbitol, diglycerol, methyl glycoside or even aldoses such as, for example, glucose or mannose.

Suitable fatty acid polyol partial esters are, for example, the glycerol or sorbitan monoesters of myristic acid, palmitic acid, stearic acid and oleic acid or of technical cocofatty acid $C_{12-18}$ cuts. Preferably, the lipophilic co-emulsifier is a glycerol ester or sorbitan ester possessing 6 to 22 carbon atoms, more preferably a glycerine mono fatty acid ester such as glycerol monooleate or sorbitan monolaurate.

Also suitable are linear and/or branched C8-22 fatty alcohols, which may optionally contain one or more double bonds in the carbon chain, and partial ethers of the polyfunctional alcohols mentioned in the description of the fatty acid polyol partial esters with C8-22 fatty alcohols.

In accordance with a preferred embodiment of the invention, the oil phase component is a methyl ester, the hydrophilic emulsifier is an alkyl polyglycoside, and the lipophilic co-emulsifier is glycerol monooleate.

The microemulsions which result are clear liquids with droplet particle sizes which are generally less than 100 nanometers. Preferably, the microemulsions are optically isotropic, with droplet particle sizes ranging from about 10 nm to about 100 nm, and are thermodynamically stable over a broad temperature range from about 0° C. to about 80° C.

The proportions of the various components of the microemulsions of the present invention generally are in the range of from about 5% to about 50% by weight oil, preferably about 25% to about 35%; about 2% to about 20% by weight hydrophilic emulsifier, preferably about 5% to about 15%, most preferably about 10%; about 2% to about 15% by weight lipophilic co-emulsifier, preferably about 5% to about 12%, most preferably about 8%; with the remainder of the microemulsion being water. The proportions of the various components of the microemulsions of the present invention can vary within the ranges above depending upon the nature of the agrochemical(s) incorporated therein. These proportions can be readily determined by those of ordinary skill in the art. Preferably, the hydrophilic emulsifier is an alkyl polyglycoside and the lipophilic co-emulsifier is glycerol monooleate ("GMO"). The preferred ratio by weight of hydrophilic emulsifier to the combined amount of hydrophilic emulsifier and lipophilic co-emulsifier is generally between about 0.60 and about 0.80.

The microemulsion may be combined and diluted with water-soluble or substantially water-soluble agrochemicals or formulated agrochemicals. The relative amounts will vary depending upon, among other things, the particular adjuvant mixture, the particular agrochemical and the particular application. Preferably, during application, a spray solution may contain from about 0.005% to about 0.5% of the microemulsion, more preferably from about 0.01% to about 0.2% of the microemulsion. The microemulsions according to the invention are distinguished in particular by their stability at low temperatures and by their unlimited dilutability. These emulsions can be diluted, for example, with 1000 times their volume of water without oily separation.

Preferred water-soluble or substantially water-soluble agrochemicals include herbicides, for example, isopropylammonium glyphosate or other glyphosate salts. Other water-soluble or substantially water-soluble herbicides may include, for example, the salt forms of phenoxy herbicides. Other agrochemicals that may be utilized in accordance with the present invention include any other available herbicides, including both water-soluble and water-insoluble herbicides, and other substances which may be used for plant protection, such as insecticides, acaricides, nematicides and fungicides.

Microemulsion adjuvants of the invention have a high tolerance for electrolytes. For example, ammonium sulfate, a common fertilizer, may be added to the adjuvants at concentrations as high as about 15 wt. % and the microemulsions will remain stable.

Furthermore, microemulsion formulations of the adjuvant may have additional advantages, including: (1) all components of the microemulsion adjuvant may be naturally derived, e.g. based on seed oils, and thus are readily biodegradable; (2) the components of the microemulsion may all be "green" chemicals and will have no special labeling or handling requirements, e.g., glycerol monooleate is approved for use in foods; and (3) the components of the microemulsion may reduce foam formation without the need for additional defoaming chemicals. For example, methyl esters are excellent defoamers.

In addition to the components described above, the microemulsion adjuvants may contain other typical auxiliaries and additives useful in agrochemical applications. These may include agents to clarify the mixture, e.g., propylene glycol, wetting agents, antifreeze agents, antifoam agents, dyes, preservatives, thickening agents, surfactants, other nonionic and cationic emulsifiers or water-soluble alcohols containing from about 1 to about 6 carbon atoms, inorganic salts and also inorganic or organic acids for stabilizing the pH value of the concentrates.

Suitable wetting agents include any of the conventional wetting agents which are well known in the art. In particular, anionic wetting agents such as sodium N-methyl-N-oleyoyl-taurate, octylphenoxy polyethoxy ethanol, nonylphenoxy polyethoxy ethanol, sodium dioctyl sulfosuccinate, sodium dodecyl benzyl sulfonate, sodium lauryl sulfonate, sodium sulfonated alkyl carboxylate and the like and mixtures thereof are preferred. Ethoxylated alcohols may also be used. Wetting agents useful in the present invention include "Tamol 731 SD," an anionic, polymer-type dispersant available from Rohm & Haas Co. of Philadelphia, Pa. Where utilized, wetting agents can be incorporated into the microemulsion composition in amounts of between about 1% and about 5% by weight (based on the total weight of all ingredients).

Antifoam agents useful in the present invention include "Surfynol 104E," a surfactant having the formula $C_{14}H_{26}O_2$ dissolved in ethylene glycol, available from Air Products and Chemicals, Inc. of Allentown, Pa. and "ANTIFOAM FG-10," a dimethylsilicone emulsion, available from Dow Chemical Company of Midland, Mich. Antifoam agents can each be incorporated into the microemulsion composition in amounts of between about 0.1% and about 0.5% by weight (based on the total weight of all ingredients). Other suitable antifoam agents for use in accordance with the present invention include modified organo silicones, and commercially available antifoam agents, for example, Tego® products available from Degussa Corp. (Hopewell, Va.).

Suitable antifreeze agents which may be used in the microemulsion adjuvants of the present invention include, but are not limited to, glycol derivatives.

The concentrates according to the invention preferably have a pH value of about 5.5 to about 7.5. Concentrates with a pH value of 6 to 7 are particularly preferred. The pH value is adjusted in particular with polyhydroxycarboxylic acids containing 2 to 6 carbon atoms and 2 to 6 hydroxyl groups, for example citric acid. These optional auxiliaries and additives are generally present in quantities of about 0.1 to about 10 wt. %.

The microemulsions according to the invention may be diluted with either deionized water or regular tap water without breaking down.

The present invention also relates to a process for the production of ready-to-use preparations containing agrochemicals, such as those described above, premixed with the microemulsion adjuvants described herein.

The concentrate microemulsions according to the invention are prepared by known methods, such as by blending the components at room temperature. The order of addition of the raw materials is not important and constitutes another advantage of this invention in comparison with other emulsions where the production process is critical.

In one embodiment, the emulsion is prepared by adding all the ingredients, except the co-surfactants, which are then slowly poured into the mixture until a transparent and clear microemulsion is obtained. The microemulsion adjuvant may then be added to an agrochemical and water, preferably just prior to application in the field.

As set forth in greater detail in the Examples below, it was found that the adjuvants of the invention acted better than commercially available adjuvants for agrochemicals. Without wishing to be bound by any theory, the methyl esters or mineral oil may be useful when added to agrochemicals to improve their penetration into the plant through the cuticles. The combination of these oils with alkyl polyglycosides, which are excellent wetting agents, and with glyceryl monooleate, which is an excellent emulsifier, may produce a synergistic effect in the microemulsion blends. In addition, the small particle size of the microemulsion, approaching about 10 to about 100 nanometers, may also improve the efficiency of the agrochemicals.

The following examples are intended to illustrate the invention without limiting it in any way.

EXAMPLES

Examples of three agrochemical microemulsions, each containing an alkyl polyglycoside as the hydrophilic emulsifier, glycerol monooleate as the lipophilic co-emulsifier and a methyl ester or mineral oil, as the oil phase, are shown below in Table 1. The emulsions were prepared as a simple blending at room temperature.

TABLE 1

| Adjuvant A |
|---|
| 32.1 wt. % methyl oleate, Agnique ® ME 181-U (Cognis) |
| 8.8 wt. % glyceryl monooleate, Agnique ® GMO (Cognis) |
| 25.0 wt. % C8-C10 alkyl polyglycoside (70% active), Agnique ® PG 8107 (Cognis) |
| 0.24 wt. % citric acid (50%) |
| 33.8 wt. % water |
| Adjuvant B |
| 29.3 wt. % methyl laurate, Agnique ® ME 1290 (Cognis) |
| 9.7 wt. % glyceryl monooleate, Agnique ® GMO (Cognis) |
| 29.8 wt. % C8-C10 alkyl polyglycoside (60% active), Agnique ® PG 8105 (Cognis) |
| 0.22 wt. % citric acid (50%) |
| 2.7 wt. % propylene glycol |
| 28.6 wt. % water |
| Adjuvant C |
| 19.6 wt. % OP6A, mineral oil. |
| 8.9 wt. % glyceryl monooleate, Agnique ® GMO (Cognis) |
| 23.2 wt. % C9-C11 alkyl polyglycoside, 50% active, Agnique ® PG 9116 (Cognis) |
| 0.5 wt. % propylene glycol |
| 47.8 wt. % water |

In order to test their adjuvant properties, Adjuvants A and B were added directly to a spray tank mixture of water and isopropylammonium glyphosate. One field test was established to evaluate their efficiency in tank mix with glyphosate in direct comparison to RoundUp® Ultra Max (Monsanto Company) on annual weeds at a ratio of glyphosate/adjuvant 1:1.962 and at different rate of glyphosate (540 to 1080 gae/ha). The annual weeds were: IAQGR (*ipomoea grandipholia*), EPHLL (*euphorbia heterophylla*), CASOB (*senna obtusifolia*), BRAPL (*brachiara plantaginea*), ECHCO (*echinichloa colonum*) and ELEIN (*eleusine indica*). Water volume used was l/ha and visual % pest control rating was taken after 21 days. Detailed results from the trials which were conducted are shown in Table 2.

TABLE 2

| Field Testing | |
|---|---|
| APPLIED Day 0 | |
| Time 8:50-9:50 AM | |
| Temp, ° C. | 20.7-22 |
| Rel Humidity | 63-56 |
| Sky | Clear |
| Water Volume | 100 liter/ha |

TABLE 2-continued

| Equipment | Backpack |
|---|---|
| Nozzle | XR110.01 |
| Pressure | 34 psi |

| Weed Species | Common Name | Abbrev | Height (cm) | Stage | Number plants/m |
|---|---|---|---|---|---|
| *Ipomoea grandipholia* | Morning Glory | IAQGR | 35 | vegetative | 20 |
| *Euphorbia heterophylla* | Wild Poinsettia | EPHLL | 50 | flowering | 60 |
| *Senna obtusifolia* | Sicklepod | CASOB | 55 | vegetative | 50 |
| *Brachiaria plantaginea* | Alexandergrass | BRAPL | 65 | vegetative | 45 |
| *Echinochloa colonum* | Junglerice | ECHCO | 60 | flowering | 80 |
| *Eleusine indica* | Goosegrass | ELEIN | 30 | flowering | 75 |

| 21 Days After Treatment | Rate | Broadleaf Weeds | | | Grasses | | |
|---|---|---|---|---|---|---|---|
| Sample | (g ae/ha) | IAQCR | EPHLL | CASOB | BRAPL | ECHCO | ELEIN |
| RU Ultra | 540 | 63.3 | 65.0 | 71.7 | 88.3 | 66.7 | 85.0 |
| RU Custom + Adj A | 540 + 275 | 78.3 | 78.3 | 85.0 | 88.3 | 66.7 | 85.0 |
| RU Custom + Adj B | 540 + 275 | 73.3 | 76.7 | 78.3 | 86.7 | 65.0 | 81.7 |
| RU Ultra | 720 | 78.3 | 86.7 | 86.7 | 96.0 | 81.7 | 96.0 |
| RU Custom + Adj A | 720 + 367 | 88.3 | 83.3 | 91.7 | 91.7 | 81.7 | 96.0 |
| RU Custom + Adj B | 720 + 367 | 85.0 | 83.3 | 91.7 | 91.7 | 80.0 | 95.0 |
| RU Ultra | 900 | 93.3 | 95.0 | 97.0 | 99.3 | 91.7 | 97.0 |
| RU Custom + Adj A | 900 + 458 | 96.0 | 98.0 | 98.0 | 98.0 | 91.7 | 97.0 |
| RU Custom + Adj B | 900 + 458 | 95.0 | 97.0 | 95.0 | 95.0 | 91.7 | 95.0 |
| RU Ultra | 1080 | 96.0 | 96.0 | 97.0 | 100.0 | 95.0 | 100.0 |
| RU Custom + Adj A | 1080 + 550 | 97.0 | 98.7 | 98.7 | 99.3 | 97.7 | 99.3 |
| RU Custom + Adj B | 1080 + 550 | 96.0 | 97.0 | 97.0 | 100.0 | 95.0 | 97.7 |

RU Ultra = RoundUp ® UltraMax
RU Custom = isopropyl ammonium glyphosate

As can be seen from the above, the microemulsion adjuvants A and B in tank mix with isopropylammonium glyphosate showed significantly better control of broadleaf weeds, 8% and 12% respectively, compared with RoundUp® UltraMax.

While the invention has been described with reference to preferred embodiments, it will be understood by those skilled in the art that various changes may be made and equivalents may be substituted for elements thereof without departing from the scope of the invention. Thus, it is intended that the invention not be limited to the particular embodiments disclosed as the best mode contemplated for carrying out this invention, but that the invention will include all embodiments falling within the scope of the appended claims.

What is claimed is:

1. A method for treating plants with an agrochemical, comprising spraying the plants with the agrochemical in combination with a micro-emulsion composition consisting of:
   (a) from about 5% to about 50% of an oil phase,
   (b) from about 2% to about 20% of a hydrophilic emulsifier selected from the group consisting of alkyl(oligo)glycosides,
   (c) from about 2% to about 15% of a lipophilic co-emulsifier selected from the group consisting of glycerol esters of C6-C22 fatty acids, and sorbitan esters of C6-C22 fatty acids, and
   (d) from about 10% to about 90% water,
wherein the ratio by weight of hydrophilic emulsifier to the combined weight of hydrophilic emulsifier and lipophilic co-emulsifier is from about 0.60 to about 0.80, and wherein said agrochemical is a water-soluble or substantially water-soluble agrochemical, whereby said micro-emulsion composition increases the field efficacy of said agrochemical over a similar method without said micro-emulsion composition.

2. The method of claim 1 wherein said oil phase is a fatty acid ester or mixture of fatty acid esters.

3. The method of claim 2 wherein said fatty acid ester is selected from the group consisting of methyl oleate and methyl laurate.

4. The method of claim 1 wherein said oil phase is selected from the group consisting of mineral oils, vegetable oils, paraffinic oils and silicone oils.

5. The method of claim 1 wherein said alkyl(oligo)glycoside corresponds to the formula:

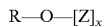

in which R is an alkyl group containing 8 to 22 carbon atoms, Z is a sugar unit containing 5 or 6 carbon atoms and x is a number from 1 to 10.

6. The method of claim 1 wherein said lipophilic co-emulsifier is selected from the group consisting of glycerol monooleate and sorbitan monolaurate.

7. The method of claim 1 wherein said agrochemical is selected from the group consisting of pesticides, herbicides, algicides, fungicides, bactericides, viricides, insecticides, aphicides, miticides, nematicides, molluscicides, plant growth regulators, fertilizers, nutrients, gametocides, defoliants, desiccants, pest repellants, synergists, herbicide safeners, salt additives, preservatives, and combinations thereof.

8. The method of claim 1 wherein said agrochemical is a glyphosate herbicide.

9. The method of claim 1, wherein said oil phase is methyloleate, and said co-emulsifier is glycerol monooleate.

10. The method of claim 8 wherein said glyphosate herbicide is a glyphosate salt.

11. A method for treating plants with an agrochemical, comprising spraying the plants with the agrochemical in combination with a micro-emulsion composition consisting of:
  (a) from about 5% to about 50% of an oil phase,
  (b) from about 2% to about 20% of a hydrophilic emulsifier selected from the group consisting of alkyl(oligo)glycosides,
  (c) from about 2% to about 15% of a lipophilic co-emulsifier selected from the group consisting of glycerol esters of C6-C22 fatty acids, and sorbitan esters of C6-C22 fatty acids,
  (d) from about 10% to about 90% water, and
  (e) one or more auxiliaries selected from the group consisting of clarifying agents, wetting agents, antifreeze agents, antifoam agents, dyes, preservatives, thickening agents, nonionic emulsifiers, cationic emulsifiers, water-soluble alcohols containing from 1 to about 6 carbon atoms, inorganic salts, inorganic acids, organic acids and combinations thereof;

wherein the ratio by weight of hydrophilic emulsifier to the combined weight of hydrophilic emulsifier and lipophilic co-emulsifier is from about 0.60 to about 0.80, and wherein said agrochemical is a water-soluble or substantially water-soluble agrochemical,
  whereby said micro-emulsion composition increases the field efficacy of said agrochemical over a similar method without said micro-emulsion composition.

12. The method of claim 11 wherein said one or more auxiliaries (e) are selected from the group consisting of citric acid, propylene glycol and mixtures thereof.